(12) United States Patent
Vanoni et al.

(10) Patent No.: US 9,103,795 B2
(45) Date of Patent: Aug. 11, 2015

(54) METHOD OF OPERATING AN OPTOCHEMICAL SENSOR

(71) Applicant: Mettler-Toledo AG, Greifensee (CH)

(72) Inventors: Claudio Vanoni, Aurigeno (CH); Francesca Venturini, Dübendorf (CH); Christoph Kleinlogel, Zürich (CH)

(73) Assignee: Mettler-Toledo AG, Greifensee (CH)

( * ) Notice: Subject to any disclaimer, the term of this patent is extended or adjusted under 35 U.S.C. 154(b) by 146 days.

(21) Appl. No.: 13/858,437

(22) Filed: Apr. 8, 2013

(65) Prior Publication Data

US 2013/0295682 A1 Nov. 7, 2013

Related U.S. Application Data

(63) Continuation of application No. PCT/EP2011/066437, filed on Sep. 21, 2011.

(30) Foreign Application Priority Data

Oct. 8, 2010 (EP) .................................... 10186924

(51) Int. Cl.
| | | |
|---|---|---|
| *G01N 21/00* | (2006.01) | |
| *G01N 21/75* | (2006.01) | |
| *G01N 21/27* | (2006.01) | |
| *G01N 21/64* | (2006.01) | |
| *G01N 21/77* | (2006.01) | |
| *G01N 21/85* | (2006.01) | |

(52) U.S. Cl.
CPC .............. *G01N 21/75* (2013.01); *G01N 21/274* (2013.01); *G01N 21/643* (2013.01); *G01N 21/77* (2013.01); *G01N 21/8507* (2013.01)

(58) Field of Classification Search
None
See application file for complete search history.

(56) References Cited

U.S. PATENT DOCUMENTS

| | | | |
|---|---|---|---|
| 6,782,297 B2 * | 8/2004 | Tabor .............................. | 700/55 |
| 7,135,342 B2 | 11/2006 | Colvin, Jr. et al. | |
| 7,375,347 B2 | 5/2008 | Colvin, Jr. et al. | |
| 2005/0236580 A1 | 10/2005 | Colvin, Jr. et al. | |
| 2007/0059210 A1 | 3/2007 | Colvin, Jr. et al. | |
| 2009/0146078 A1 | 6/2009 | Colvin, Jr. et al. | |
| 2010/0032583 A1 | 2/2010 | Kane | |
| 2010/0063762 A1 | 3/2010 | Pechstein et al. | |
| 2010/0253934 A1 | 10/2010 | D'Ascenzi et al. | |
| 2011/0064617 A1 | 3/2011 | Colvin, Jr. et al. | |

FOREIGN PATENT DOCUMENTS

WO 02090951 A1 11/2002

* cited by examiner

*Primary Examiner* — Robert Xu
(74) *Attorney, Agent, or Firm* — Standley Law Group LLP

(57) ABSTRACT

An optochemical sensing device has source that emits radiation of a first and a second predetermined intensity, a detector, and a sensitive element that comprises a signal substance. To measure an analyte in a measurement medium, the sensitive element is contacted with the analyte. A first raw signal, which is dependent on the analyte content is obtained by exciting the signal substance with radiation of the first predetermined intensity. At a later time, a second raw signal is also obtained. A comparison of the raw signals yields a comparison value, which is compared against a predetermined limit value. If the comparison value exceeds the limit value, the radiation source is set at the first intensity. If the comparison value is smaller than the limit value, the radiation source is set at the lower second intensity. Using the lower radiation intensity prolongs the life of the sensitive element.

7 Claims, 6 Drawing Sheets

METHOD OF OPERATING AN OPTOCHEMICAL SENSOR

CROSS-REFERENCE TO RELATED APPLICATIONS

This application is a continuation of, and makes a claim of priority to, PCT/EP2011/066437, which was filed 21 Sep. 2011, which designates the United States, and which claims priority to European patent application 10186924.6, which was filed on 8 Oct. 2010. Both the PCT and the European application are incorporated by reference as if fully recited herein.

TECHNICAL FIELD

The disclosed embodiments relate to a method of operating an optochemical sensor, and they also concern a sensor that is operable to carry out the method.

BACKGROUND

Optochemical sensors find application for the determination of a wide diversity of analytes in the laboratory as well as in process systems. For example in a process, optochemical sensors based on the principle of fluorescence quenching can be used for the determination of gases that are dissolved in a fluid, such as for example oxygen or carbon dioxide. To perform this function, the sensor includes a sensitive element with a signal substance that is capable of interacting with the analyte. Under the principle of fluorescence quenching, the molecules of the signal substance are excited by irradiation with light of a suitable wavelength. As the molecules return from the excited state to their basic state, they release the absorbed energy again in the form of fluorescence, whereupon the latter is quenched by interaction with the analyte. For the detection of the fluorescence-quenching effect, it is important that the fluorescence has sufficient intensity or energy which is commensurate with the intensity of the irradiation.

In principle, it is possible to determine many other analytes in a fluid measurement medium by fluorescence quenching, as long as the signal substance, for example a fluorophore, is sensitive in regard to the analyte of interest. The term "fluid" in this context encompasses liquids and gases as well as mixtures thereof.

These sensors, which contain a signal substance, have the disadvantage that independent of the field of application and, in particular independent of the measurement medium, the fluorescence of the signal substance will weaken over time, and thus the intensity of the fluorescence-quenching effect will drop off. The decline of the fluorescence can for example be caused by the radiation being used for the measurement as well as by the cleaning methods that are employed, such as for example autoclaving or the conventional CIP- and/or SIP processes (cleaning in place, sterilizing in place). As a means to compensate for the decline in fluorescence and the associated deterioration of the measurement results, optochemical sensors operating according to this method often have exchangeable sensitive elements. While an exchange of the sensitive element restores the functionality of the sensor, it can disrupt the production process, in particular by causing additional work and causing interruptions in the reaction or process. Interruptions for the exchange of the sensor or the sensitive element may in some cases involve substantial costs and extensive efforts, especially if the sensor is installed at a less accessible location of the process system.

The aging of the sensitive element not only dictates the time for the exchange, but with advancing time in operation also comes a deterioration of the measurement accuracy of the sensitive element, which can lead to errors in the measurement results. Furthermore, in particular sensors with older sensitive elements will need to be calibrated by the user more often in order to ensure the quality and reproducibility of the measurement results.

Several known methods exist, whereby the aging of the sensitive element can be slowed down. For example, the intensity of the irradiation can be reduced, but this will cause an increase in the noise content of the raw signal, as the intensity of the fluorescence-quenching effect is being reduced at the same time. A stronger or increased noise level has the consequence that in particular lower concentrations of an analyte can no longer be determined with sufficient accuracy or cannot be determined at all. The noise could be reduced simply by taking an average over several raw or processed signals or processed signals, but this would affect, i.e. slow down, the response of the sensor. In other words, the sensor would take a longer time to react to a change of the measurement medium.

The term "raw signal" refers to the signal in its original condition as delivered by the detector. The raw signal, which is a function of the analyte content, can subsequently be converted into a processed signal which is either released directly in the form of a measurement value or can be converted further into a measurement value.

As a further possibility, the sampling rate of the measurement can be slowed down, so that the individual raw signals are separated by longer time intervals. This solution likewise slows down the response of the sensor, as fast changes or fluctuations of the analyte content in the measurement medium can hardly be detected anymore, especially if a change of the measurement medium occurs within the time between two measurement updates. Also, the sampling period can be varied only within a limited range from about 1 to 30 seconds, as the response time of the sensor would otherwise be affected too much.

It is further possible to compensate for the aging effect through arithmetic measures in the processing of the raw signals. However, the aging, more precisely the degree of aging, is specific to every application in which the sensor is being used, as the conditions to which the sensor is exposed, for example the measurement medium, analyte content, temperature, pressure, cleaning methods and/or frequency of cleaning, depend on the application. Consequently, an individual correction- or compensation function would have to be determined, implemented in a software program, and executed for each application, but with the multitude of possible applications where such sensors are used, this concept is virtually impossible to realize.

For example in US 2010/063762 A1, a method of establishing the operating life or a calibration period of a sensor is disclosed which is based on the determination and evaluation of forecast values or forecast intervals that are related to the actual service conditions of the sensor.

In US 2010/0032583 A1, a system is disclosed in which the physical location where the incident radiation meets the sensitive element can be varied and, in addition, the intensity of the incident radiation can be adjusted. This allows the magnitude or intensity of the fluorescence response to be kept at a constant level. On the one hand, as the sensitivity declines, the intensity of the incident radiation is simply raised or adjusted. On the other hand, the sensitive element can be used over a longer time period, as the position of the incident radiation relative to the sensitive element can be changed, if a currently used location on the sensitive element has been worn out to a degree where the measurement result is affected. This concept has the drawback that additional means are required in the sensor for the positioning of the incident radiation. This increases the complexity of the sensor and also makes the sensor less robust, because arrangements for shifting or adjusting an optical light path are very susceptible to mechanical stress.

Therefore, the task presents itself to develop a method for the operation of an optochemical sensor which allows the measurement performance of the sensor to be improved, wherein in addition the sensor is to maintain an unchanging level of measurement accuracy without a significant change in response time essentially independent of the aging of its sensitive element. In addition, the method should allow the sensitive element to operate with the highest possible efficiency at the lowest possible radiation exposure level.

SUMMARY

This task is solved by a method for the operation of an optochemical sensor which comprises a housing, a radiation source, a detector, and a sensitive element. The radiation source and the detector are arranged in the housing of the sensor. Furthermore, the sensitive element comprises a signal substance which, after an interaction with an analyte, can be excited by the radiation source. The method of operating this optochemical sensor includes several steps.

First, the sensitive element is brought into contact with the analyte, so that the signal substance can interact with the analyte. Next, the signal substance is excited by the radiation source with radiation of a first intensity. Based on the respective radiation response, a first raw signal is determined at a first point in time, and a second or further raw signal is subsequently determined at a second or further point in time, wherein the first, second and/or further raw signal represents a function of the analyte content. Next, at least one comparison value is calculated which depends on at least two or more raw signals. Then, the radiation intensity is evaluated and adjusted based on a comparison of the at least one comparison value to at least one predetermined limit value.

For the evaluation and adjustment of the radiation intensity, the at least one comparison value can be compared to the at least on limit value. If the comparison value is greater than or equal to the limit value, the radiation is set to or adapted to the level of the first radiation intensity. If the comparison value is smaller than the limit value and accordingly the analyte content is essentially stable, a second radiation intensity is set which is lower than the first radiation intensity.

The second radiation is smaller than the first radiation intensity, so that the radiation exposure level of the sensitive element is reduced by the foregoing method as long as the sensor produces stable raw signals and the measurement medium, in particular the analyte content, is essentially stable. With preference, the method is operated initially with the higher radiation intensity, i.e. the first or starting intensity, which is adapted in the course of the process, dependent on the relationship that is found between the comparison value and the limit value. The method can be continued until a termination criterion has been met.

The limit value that is being used is preferably dependent on the selected radiation intensity level, so that different limit values are predetermined for the first radiation intensity or for a further radiation intensity. The limit value represents a measure for an allowable change of the analyte content within which the latter is considered to be stable. The steps of determining further raw signals, determining the comparison value, as well as the subsequent steps, can be repeated until a given termination criterion has been met.

The term "measure for the allowable change in analyte content" means a value or a range within which the analyte content is essentially stable and does not change significantly. The limit value can either be specified at the factory for a sensor or for a certain application, or it can be set by the user.

This method is very advantageous, because the radiation intensity can always be adapted to the currently existing conditions in the measurement medium, and the radiation exposure of the sensor, in particular of the sensitive element, can be minimized. Thus, by using this method, the measurement accuracy of the sensor can be preserved over the long term or at least over a longer time period without an exchange of the sensitive element, and changes in the analyte contact can be met quickly by adjusting the radiation intensity.

The calculation of a comparison value can be based on an individual raw signal and/or a plurality of raw signals and/or on processed signals which are calculated from the raw signals. The comparison value preferably comprises a function of the current raw signal and of the average of the preceding processed signals, or a function of the average of the current and the preceding processed signals and of an average of the preceding processed signals. The comparison value thus represents a measure for the change of the current raw signal relative to the preceding signal or signals and/or raw signals, and by comparing the comparison value to the at least one limit value, conclusions can be drawn about the stability and or the change of the analyte content.

Accordingly, the illumination or irradiation of the sensitive element, and thus the radiation intensity, is adaptively matched to the conditions that exist in the measurement medium, so that as long as the raw signals are essentially constant, indicating an essentially stable analyte concentration, the measurements can be performed with a low radiation intensity, and as soon as a change appears, the measurements can be performed with a higher radiation intensity. In this way, the overall amount of radiation exposure of the sensitive element is reduced, because the radiation is set to the higher intensity level only when there is a change in the measurement medium, specifically in the analyte content, and therefore raw signals of a higher signal strength and quality are needed. As long as the analyte content is essentially stable and shows no significant change, it is in most cases sufficient to determine the raw signals at the lower radiation intensity and a somewhat reduced signal quality.

The switch from the first to the second, lower radiation intensity can be made for example when the phase shift of the measured raw signals is low, i.e. when the predetermined limit value is not exceeded. As long as the raw signal, and thus the analyte content in the measurement medium, remains essentially stable, the measured phase deviation is essentially constant.

In a further embodiment, the method can further encompass as an additional step the evaluation and adaptation of a smoothing factor which enters into at least one filter function for the conversion of the raw signals into processed signals and/or measurement values.

An adaptation of the smoothing factor has the effect of strengthening or weakening the filter function. In this manner, the raw signals can be converted into processed signals with essentially the same signal-to-noise ratio independent of the radiation intensity being employed.

In a further embodiment, the smoothing factor can be selected dependent on the radiation intensity that has been set, so that, for each radiation intensity being used, a specific smoothing factor is predetermined and the influence of different radiation intensities on the signal strength of the raw signals can be compensated arithmetically.

A filter function that is adapted to the selected radiation intensity and/or a specifically adapted smoothing factor is particularly advantageous because, among other benefits, it allows a reduction of noise which would manifest itself more strongly with a reduction of the radiation intensity alone. Using the first, higher radiation intensity produces raw signals which are comparatively less blurred by noise than those that are obtained with the second, lower radiation intensity. The first filter function can therefore be designed to provide a weaker degree of smoothing of the raw signals than the second filter function without affecting the response time or the measurement accuracy of the sensor.

In a further embodiment, the method of operating the optochemical sensor comprises a series of steps. First, the sensitive element is brought into contact with the analyte, so that the signal substance can interact with the analyte. Next, the signal substance is excited by the radiation source with radiation of a first intensity. Based on the respective radiation response, a first raw signal is determined at a first point in time, and a second or further raw signal is subsequently determined at a second or further point in time, wherein the first, second and/or further raw signals represent a function of the analyte content. Next, at least one comparison value is calculated which depends on at least two or more raw signals. Then, based on a comparison of the at least one comparison value to at least one predetermined limit value, the smoothing factor contained in a filter function is reviewed. The smoothing function serves to convert the raw signals into processed signals and/or measurement values. If the first comparison value is greater than or equal to the first limit value, the smoothing factor is adjusted and the radiation is set to the level of the first radiation intensity. On the other hand, if the first comparison value is smaller than the first limit value, a second comparison value is calculated and the smoothing factor and/or the setting of the radiation intensity is evaluated and adapted based on a comparison between the second comparison value, which is dependent on at least two or more raw signals, and a predetermined second limit value.

The steps of determining a second or further raw signal, of calculating the comparison value, as well as the subsequent steps can be repeated until a given termination criterion has been met.

The concept of calculating and using two comparison values is advantageous because it allows rapid as well as slow changes of the measurement medium to be detected and taken into account. As long as the measurement medium and in particular the analyte content is not stable, the higher, first radiation intensity is used, because the raw signals collected with the first radiation intensity have a better signal-to-noise ratio due to the higher radiation intensity.

The raw signals can again be converted into processed signals and/or measurement values by means of the filter function.

To evaluate and adjust the smoothing factor and/or the radiation intensity, the second comparison value can be compared to the second limit value. If the second comparison value is greater than or equal to the second limit value, the smoothing factor is raised by a given increment, whereby the effect of the filter function is lowered.

If the second comparison value is smaller than the second limit value, the smoothing factor is lowered by a given increment, whereby the effect of the filter function is increased. In addition, the smoothing factor is compared to a reference smoothing factor. If the new smoothing factor is larger than the reference smoothing factor, the subsequent measurements and calculation are performed with the new smoothing factor. If the smoothing factor is smaller than or equal to the reference smoothing factor and the analyte content is essentially stable, not only is the smoothing factor reduced by one increment, but in addition the radiation intensity is adjusted to the level of the second radiation intensity, the latter being smaller than the first radiation intensity.

The calculation of a comparison value can be based on one or more raw signals and/or processed signals. The first comparison value preferably includes a function of the current raw signal and of the average of the preceding processed signals, or a function of the average of the current and the preceding processed signals. The second comparison value preferably includes a function of an average of the current processed signal and the preceding processed signals and of an average of the preceding processed signals.

A processed signal can be calculated from a raw signal by means of at least on filter function, wherein further mathematical calculations, for example conversions, can enter into the calculation of the processed signal.

In an exemplary embodiment of the inventive method, a first, second and/or further filter function is employed, which is selected dependent on the radiation intensity that is being used. It is particularly advantageous if the filter functions are essentially identical and are only distinguished from each other by their respective filter strengths, in particular only by their smoothing factors, for example the number of raw signals over which the average is taken. When a high radiation intensity is used, a weaker filter function can be used than with a lower radiation intensity.

For the calculation of comparison values, raw signals can be used or can enter into the calculation.

The raw signals are preferably collected at a constant detection rate, so the individual raw signals are separated by equal time intervals. In this way, when carrying out the disclosed method, the response time remains largely unaffected by changes of the process parameters or of the measurement medium.

The first and/or second filter function can preferably include an exponential smoothing, wherein the selection of the smoothing factor depends on the first or second radiation intensity being used. This method of smoothing is stable and easy to implement.

As a further feature, the raw signals, the processed signals, the at least on comparison value, the at least one limit value, the at least one filter function as well as the smoothing factors can be written into or read back from a read/write memory that is connected to the sensor.

In addition the remaining service life of the sensitive element, which in comparison to conventional sensors is considerably lengthened by the use of the inventive method, can be calculated or estimated as a function of the radiation intensity being used.

A further aspect of the invention concerns an optochemical sensor that is equipped to carry out the method. The sensor includes a housing, a radiation source, a detector, and a sensitive element, wherein the radiation source and the detector are arranged in the housing and wherein the sensitive element includes a signal substance which, after an interaction with an analyte, can be excited by the radiation source, so that raw signals can be captured by the detector, wherein the raw signals are a function of the analyte content. The sensor is distinguished by the fact that the radiation source generates radiation of a first radiation intensity and of at least one second radiation intensity which are selected by comparing a comparison value to a limit value, wherein the latter represents a measure for the allowable amount of change in analyte content. The optochemical sensor can further include a processor and/or cooperate with a processor in which at least one filter function is stored, by means of which the first, second and/or further raw value can be converted into a first, second and/or further processed signal. In addition, the processor preferably includes a read/write memory.

Preferably, the current raw value is smoothed with at least one filter function which is selected based on the radiation intensity being used and which preferably includes a smoothing factor that depends on the radiation intensity.

The sensor preferably serves for determining the concentration of at least one analyte in a fluid measurement medium.

The signal substance can include an oxygen-sensitive fluorophore, and the sensor can be designed for oxygen measurements.

A further aspect of the invention concerns a measuring instrument with a sensor and with a processor in which a software program is stored which is designed to execute the method.

BRIEF DESCRIPTION OF THE DRAWINGS

Different variations of the method and of the optochemical sensor will be described in more detail on the basis of the attached drawings, wherein elements that are identical from one drawing figure to another carry the same reference symbols, and wherein.

DETAILED DESCRIPTION OF THE DRAWINGS

Figure 1:
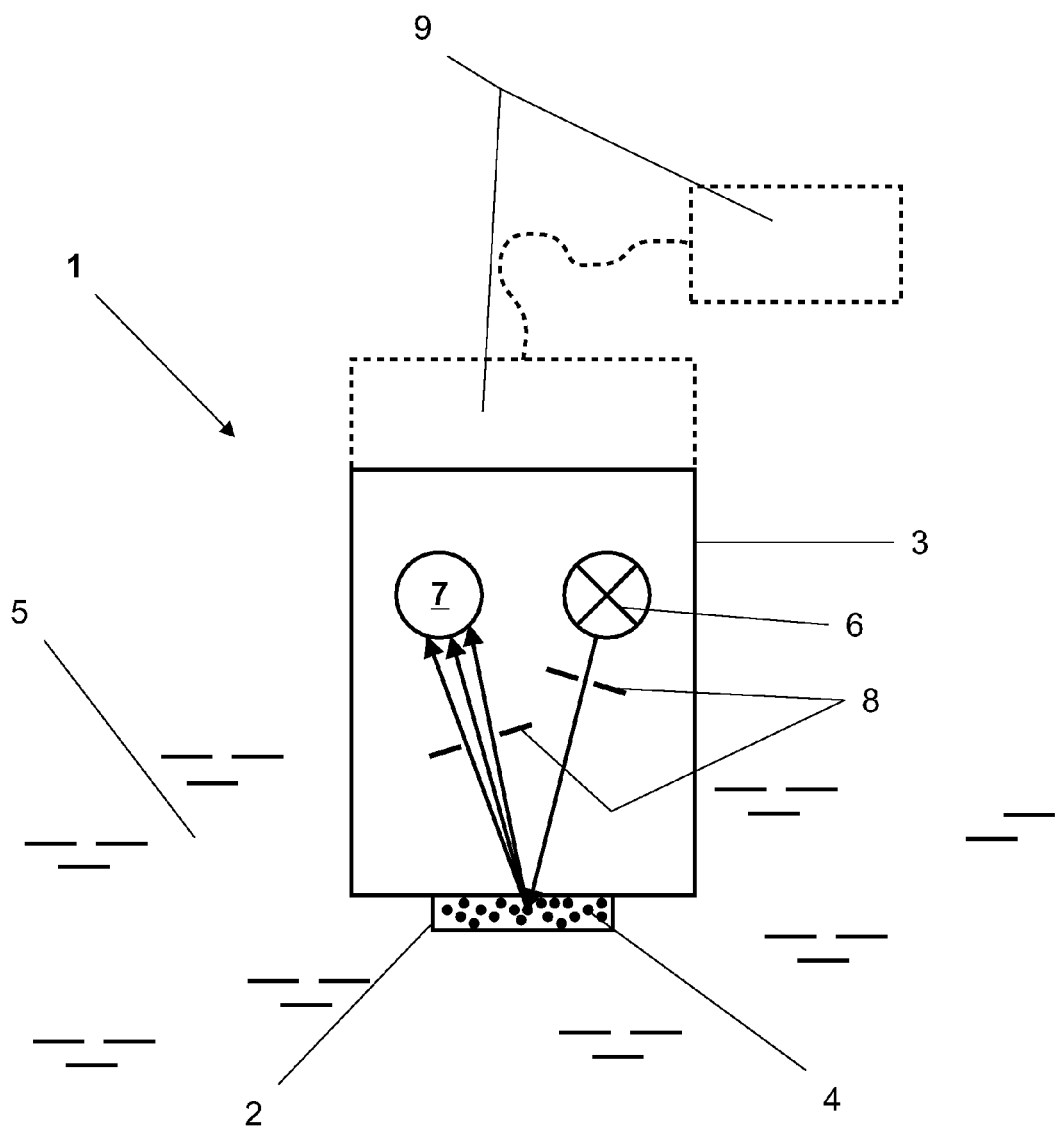
FIG. 1 schematically illustrates an optochemical sensor with a sensitive element that comprises a signal substance.

FIG. 1 illustrates an optochemical sensor 1 which includes a sensitive element 2. The sensitive element 2 is releasably connected to a sensor housing 3, so that the sensitive element 2 can be exchanged when the sensitive element or a signal substance 4 contained in it is used up or aged. In operation, as indicated here, the sensitive element 2 is in direct contact with the measurement medium 5. The sensitive element 2 can be for example a matrix of a polymeric or ceramic material in which the signal substance 4, in particular a fluorophore, is dissolved or embedded.

Arranged inside the sensor housing 3 are a radiation source 6 and a detector 7. The radiation emitted by the radiation source 6 is directed by suitable optical elements 8 (indicated only symbolically in the drawing) such as filters, mirrors, screens or lenses onto or into the sensitive element 2, where the radiation can interact with the signal substance 4. Next, the response signal is directed to the detector 7, where it is detected. For the control and processing of the detected signals, the sensor 1 also includes a control- and/or regulation unit 9 which can be arranged either as an external unit or also entirely or in part inside the sensor housing. The control- and/or regulation unit 9 can have a wire-bound or wireless connection to the sensor. The state of the art includes different variants of the control- and/or regulation unit; the latter is therefore only symbolically indicated.

Figure 2:
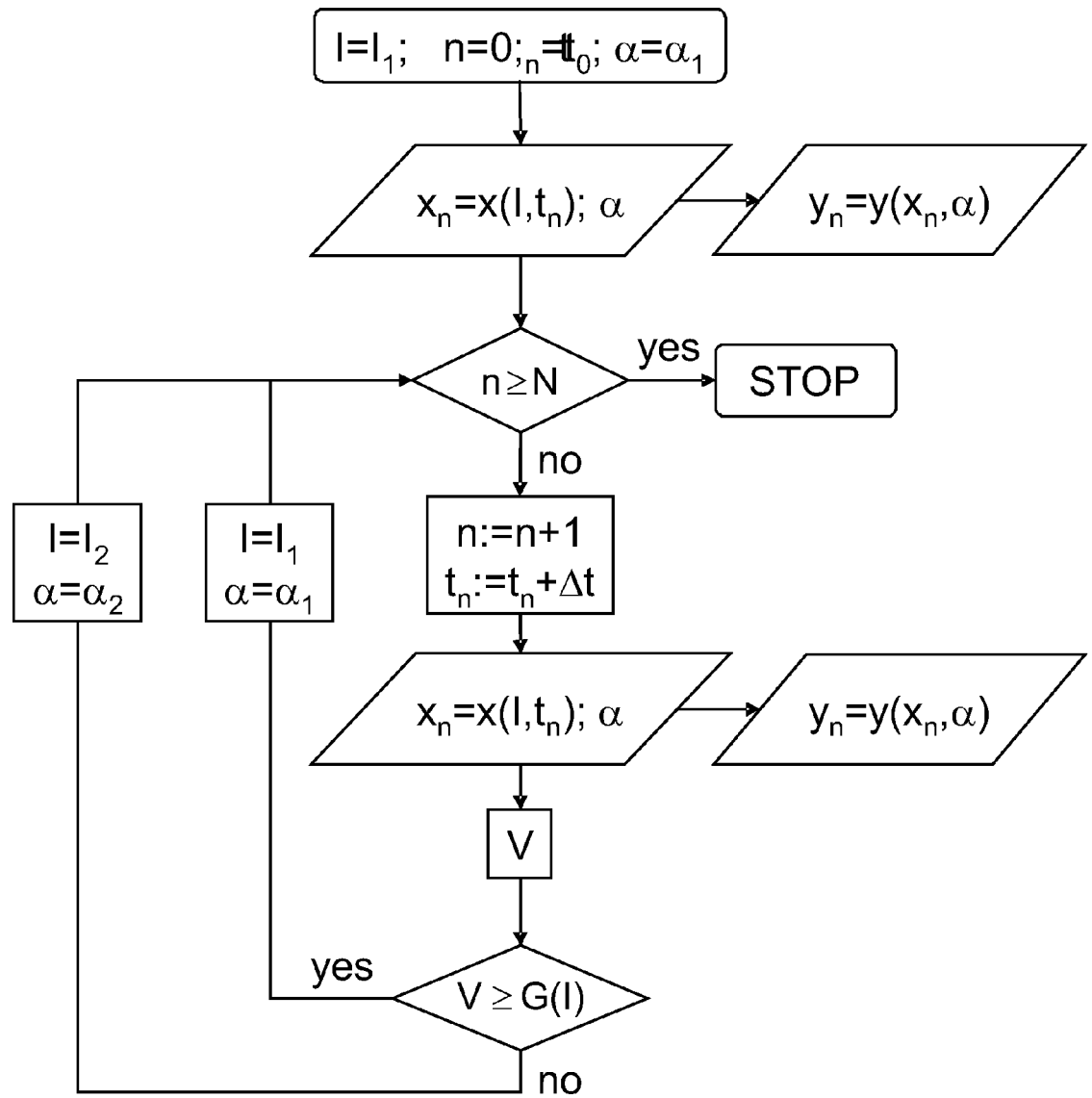
FIG. 2 is a flowchart of an embodiment of the method.

FIG. 2 illustrates a method in the form of a flowchart. At the beginning of a measurement, the optochemical sensor is excited with radiation of a first radiation intensity $I=I_1$, and at a first point in time $t_{n,n=0}$, a first raw signal $x_{n,n=0}$ is collected. This first raw signal $x_{n,n=0}$ represents a function of at least the analyte concentration in the measurement medium, the intensity I of the incident radiation and the point in time $t_{n,n=0}$ of the measurement. Based on the first raw signal $x_{n,n=0}$ a first processed signal $y_{n,n=0}=y(x_{n,n=0},\alpha)$ which can either be released directly as a measurement value or converted into a measurement value can be determined by means of a filter function. The filter function includes a smoothing factor $\alpha$ whose value depends primarily on the radiation intensity I that is being employed.

The count n is continuously incremented the longer the measurement proceeds, wherein the end of the measurement can be set by the user as well as by the measurement medium being investigated. As an example, the measurement may be terminated at or shortly after the end of a process or reaction. The termination is represented here by the interrogation of the termination criterion $n \geq 0$. If the termination criterion is met, the measurement is stopped.

If the termination criterion is not yet met, the counter is raised from n to n+1, and a second or further raw signal $x_{n,n:=n+1}$ is collected at the time $t_{n,n:=n+1}=t_n+\Delta t$, from which a further processed signal $y_{n,n:=n+1}=y(x_{n,n:=n+1},\alpha)$ is calculated.

Subsequently, at least one comparison value V is determined. This comparison value V can for example include a relationship between at least two chronologically separate raw signals or a relationship between raw signals that have been altered or processed through further mathematical operations or functions. The raw signals may have been processed in different ways. Possible treatments of a raw signal include for example smoothing with a smoothing function, averaging over a plurality of raw signals, or calculating a time derivative. These possibilities of processing a raw signal are mentioned here only as examples. There are, of course, further mathematical functions and/or operations that can be used to process raw signals.

The comparison value V is preferably determined as a function of at least the current raw signal $x_n$ and the preceding processed signal $y_{n-1}$. In addition, a comparison value V can be calculated using an average value of all or a part of the preceding raw signals $x_n, x_{n-1}, \ldots, x_0$ or processed signals $y_n, y_{n-1}, \ldots y_0$, wherein the current raw signal $x_n$ and/or the current processed signal $y_n$ can likewise be used for the calculation of the average. Furthermore, a current raw signal $x_n$ and/or a current smoothed or processed signal $y_n$ can be compared to an individual smoothed or processed signal or a series or average of smoothed or processed signals $y_n$, $y_{n-1}, \ldots, y_0$ preceding the current signal.

After the comparison value V has been determined, it is compared to at least one predetermined limit value G, wherein the selection of the latter is dependent on the radiation intensity I being used. The limit value G is preferably a constant and can be specified at the factory for each sensor or type of sensor, or can be selected by the user based on the nature of the application. It is conceivable for example that in the case of an unknown or unstable reaction the limit value or range of limit values is selected narrower than in the case of a known, stable reaction. The limit value or limit value range can thus be adapted to the sensor being used and/or to the conditions under which the measurement takes place.

Accordingly, the limit value represents a measure for the allowable amount of change in analyte content within which the analyte content is considered to be essentially stable.

If the comparison value V is larger than or equal to the limit value B, measurements are continued with the first radiation intensity $I_1$. If on the other hand the comparison value V is smaller than the limit value, the radiation intensity is reduced to the level of a second radiation intensity $I_2$, wherein $I_2 < I_1$, and subsequent measurements are performed with the second radiation intensity $I_2$. In his case, the measurement medium exhibits an essentially stable behavior, so that the sensor can be operated at a lower radiation intensity.

The adaptive switch between radiation intensities which is based on the comparison value V and thus on the current raw signals $x_n$ goes together with an adaptation of the smoothing factor $\alpha$. To maintain the quality of the measurements, in particular the signal-to-noise ratio, in spite of the change of radiation intensity, a second smoothing factor $\alpha_2$ is entered into the same or a different filter function when the second radiation intensity $I_2$ is used, and subsequent processed signals $y_n$ are calculated with the second smoothing factor $\alpha_2$ which, in comparison to the first smoothing factor $\alpha_1$ that is used with the first radiation intensity $I_1$, has a stronger smoothing effect on the raw signals $x_n$.

The cycle of determining the raw signal, calculating the processed signal and the comparison value, comparing the comparison value to the limit value and adapting the radiation intensities is repeated until the termination criterion $n \geq N$ has been met.

Figure 3:
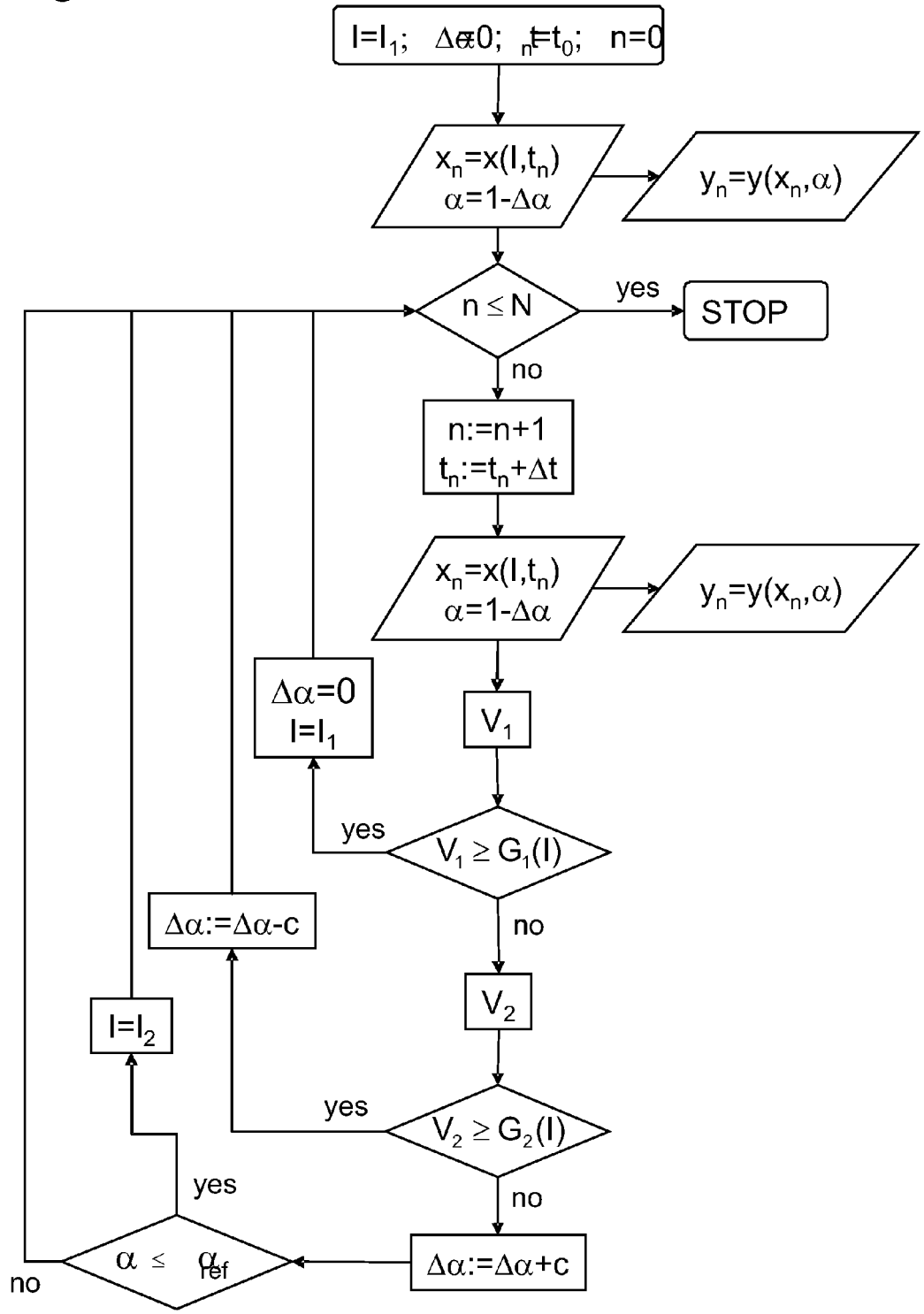
FIG. 3 is another flowchart of another embodiment of the method.

FIG. 3 illustrates by way of a flowchart a further method which differs from the method shown in FIG. 2 in particular by the fact that in addition to the adaptive change of the radiation intensity I, the adaptive change of the smoothing factor $\alpha$ likewise enters into the method. As has already been described above, with the first radiation intensity $I_1$ selected, a first and at least a second or further raw signal $x_n$ are collected or measured at a first, second and/or a further time $t_n$. Based on each of these raw signals $x_n$, a processed signal $y_n$ is calculated by means of at least one filter function. The at least one filter function contains in each case a smoothing factor $\alpha = 1 - \Delta\alpha$ which is selected dependent on the radiation intensity I being used and also dependent on the stability of the raw signal $x_n$, and thus dependent on the stability of the measurement medium.

After the first and at least one second raw signal $x_{n-1}$, $x_n$ have been collected, a first comparison value $V_1$ is determined and compared to a predetermined first limit value $G_1$ which represents a measure for the allowable deviation of the analyte content and wherein the magnitude of the first limit value $G_1(I)$ also depends on the selected radiation intensity I. The first comparison value $V_1$ can be determined as a function of at least the current raw signal $x_n$ and the preceding processed signal $y_n$ or an average of the preceding processed signals y, wherein the smoothing factor used in the calculation of the processed signals conforms to the condition $0 \leq \alpha \leq 1$. The first comparison value $V_1$ preferably includes a function of the current raw signal $x_{n-1}$ and of the average of the preceding processed signals $y_{n-1}, \ldots, y_0$.

If the first comparison value $V_1$ is greater than or equal to the first limit value G1, the raw signal $x_n$ is unstable, and the measurement medium, more specifically its analyte content, is for example undergoing a change at this moment. In this case, the first radiation intensity value $I_1$ is set or maintained for the next following raw signal measurement $x_{n,n:=n+1}$, and the smoothing factor $\alpha = 1 - \Delta\alpha$ is set at $\Delta\alpha = 0$, so that the raw signal is in essence not being smoothed in the calculation of the processed signal.

If on the other hand the first comparison value $V_1$ is smaller than the first limit value, a second comparison value $V_2$ is calculated and compared to a second limit value $G_2(I)$. The calculation of the second comparison value $V_2$ can be based on a current average value which includes the current as well as the preceding raw signals $x_n, x_{n-1}, \ldots x_0$ or the current and the preceding processed signals $y_n, y_{n-1}, \ldots, y_0$, and the preceding average which includes the preceding raw signals $x_n, x_{n-1}, \ldots x_0$ or the preceding processed signals $y_n, y_{n-1}, \ldots, y_0$. The second comparison value $V_2$ preferably includes a function of an average over the current and preceding processed signals $y_n, y_{n-1}, \ldots, y_0$ and of an average over the preceding processed signals $y_{n-1}, \ldots, y_0$.

The second limit value $G_2$ represents a measure for the allowable change of the analyte content and, in addition, depends on the selected radiation intensity I. The limit values $G_1, G_2$ are constants which can be specified for example at the factory for each sensor or sensor type.

The first comparison value $V_1$ thus serves for a quick check of the stability of the measurement medium. The second comparison value $V_2$ is more precise and serves for a closer evaluation of the stability of the measurement medium. Of course, it would also be conceivable that the first and the second comparison value $V_1, V_2$ represent one and the same value which is compared to two different limit values $G_1, G_2$.

If the second comparison value $V_2$ is greater than or equal to the second limit value $G_2$, the subsequent measurements are taken at the same radiation intensity I, but the calculation of the processed signals is performed with a larger smoothing factor $\alpha = 1 - \Delta\alpha$ with $\Delta\alpha := \Delta\alpha - c$, i.e. with a smaller amount of smoothing. The smoothing factor $\alpha$ can take on values between 0 and 1, wherein a smaller smoothing factor $\alpha$ indicates a greater amount of smoothing.

If the second comparison value $V_2$ is smaller than the second limit value $G_2$, the raw signal $x_n$, and thus the measurement medium, is essentially stable. In this case, a test is made as to whether the smoothing factor $\alpha$ has already reached equality with a reference smoothing factor $\alpha_{ref}$.

If the current smoothing factor $\alpha$ is larger than the reference smoothing factor $\alpha_{ref}$, the smoothing is made stronger by further reducing the smoothing factor $\alpha = 1 - \Delta\alpha$ with $\Delta\alpha := \Delta\alpha + c$.

If on the other hand, the current smoothing factor $\alpha$ is smaller than the reference smoothing factor $\alpha_{ref}$ and the analyte content is essentially stable, the smoothing is made stronger with $\alpha = 1 - \Delta\alpha$ wherein $\Delta\alpha := \Delta\alpha + c$, and in addition the radiation is set to the level of a second radiation intensity $I_2$ which is lower, i.e. weaker, than the first radiation intensity $I_1$.

The cycle of determining the raw signal, calculating the processed signal and the comparison value, comparing the comparison value to the limit value and adapting the radiation intensities is repeated until the termination criterion $n \geq N$ has been met.

Figure 4:
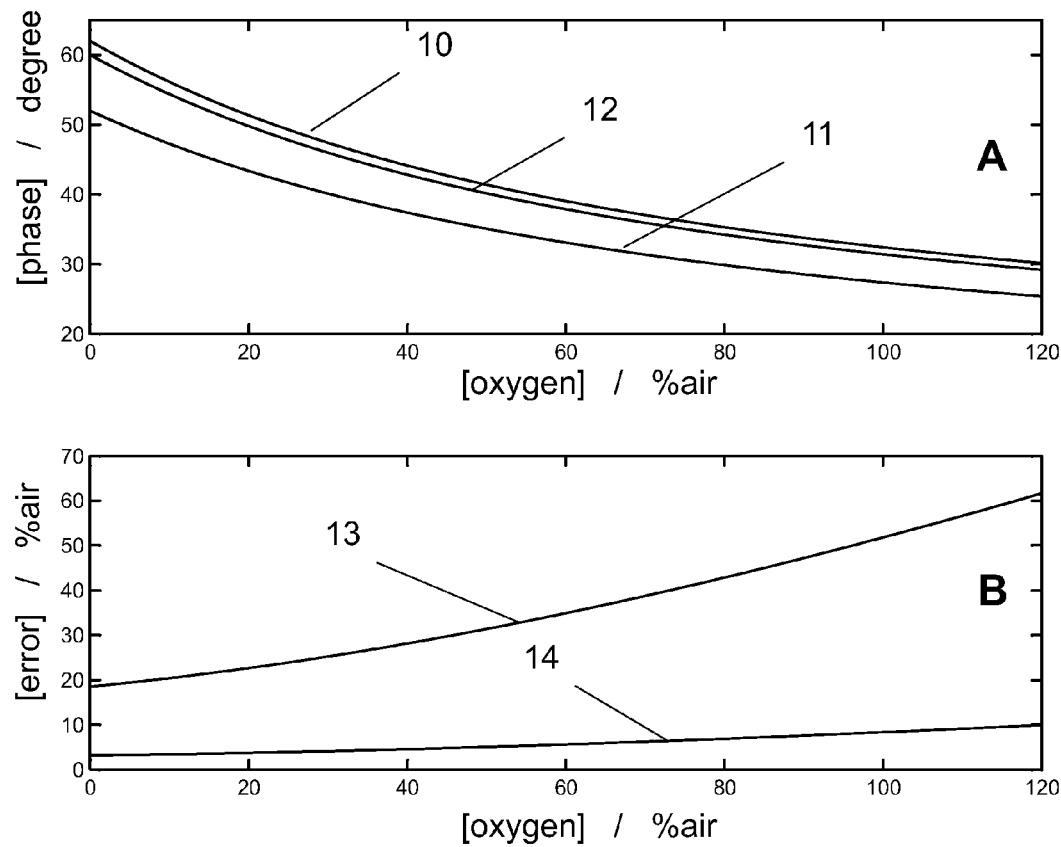
FIG. 4 shows a comparison of the aging effects manifesting themselves in the raw signals of a sensor being operated, respectively, with a conventional method and with a method according to the invention.
Figure 5:
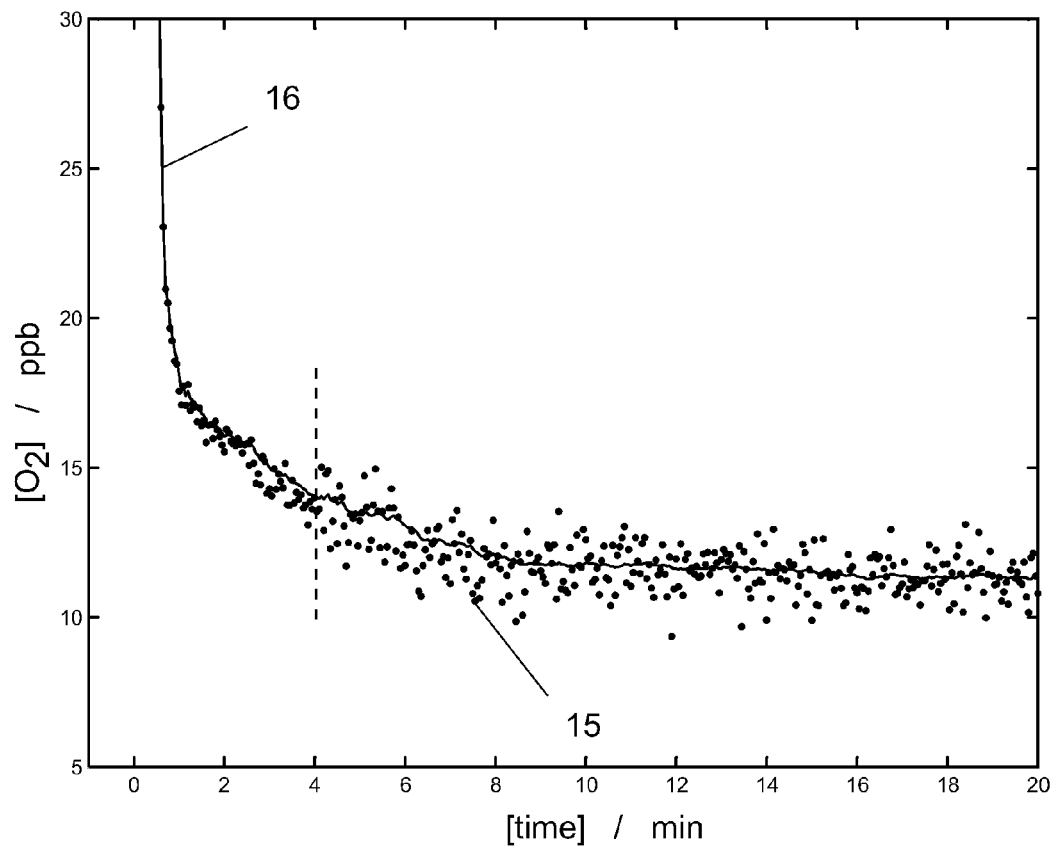
FIG. 5 shows the raw signals and the processed signals for comparison in a diagram.
Figure 6:
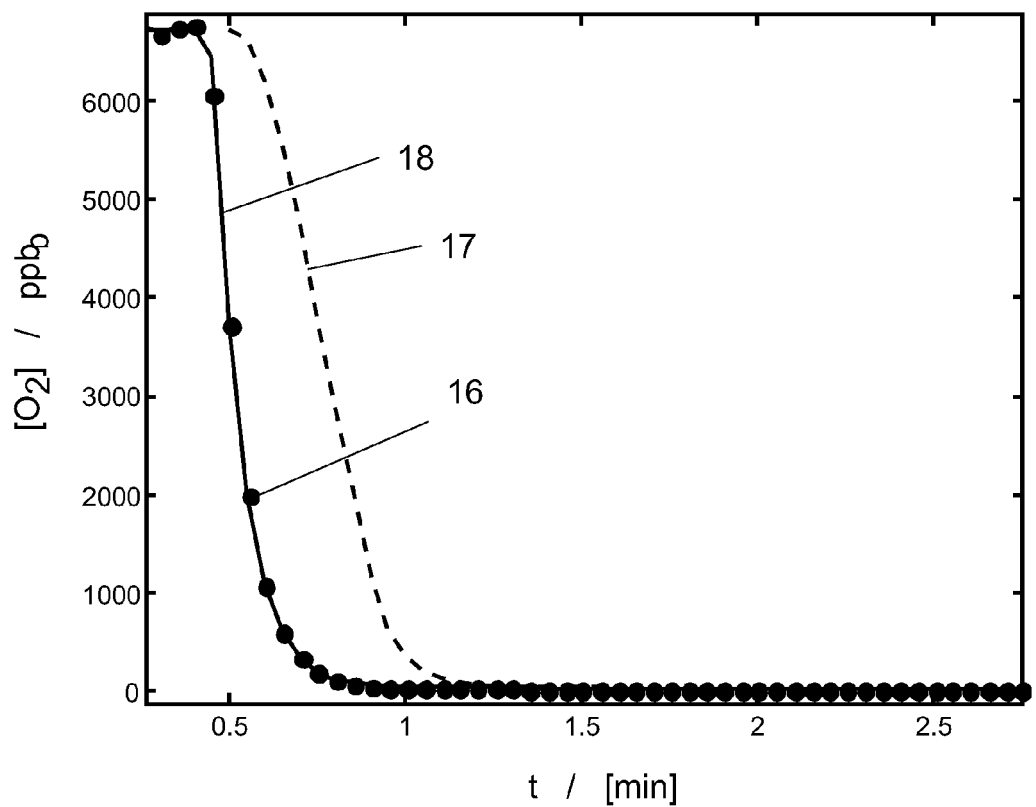
FIG. 6 shows a concentration vs. time diagram for comparison of a measurement graph obtained with the method according to the invention and a measurement graph obtained with one of the conventional methods.

The benefits of the concept of adaptively changing the radiation intensity I and/or the smoothing factor $\alpha$ are illustrated by the diagrams in FIGS. 4 to 6.

In FIG. 4, the curves in diagram A represent the phase angle as a function of concentration, and the curves in diagram B represent the measurement error as a function of concentration. The graphs demonstrate the advantages of the method over the conventional method through a comparison to measurements taken with a fresh sensitive element.

The curves in diagram A were recorded with a sensor of the type InPro6870i by Mettler-Toledo and represent the relationship of the phase angle against the oxygen concentration. The principal configuration of a sensor of this type is schematically illustrated in FIG. 1. The InPro6870i sensors are precalibrated sensors for which a relatively small measurement error of about ±1% is specified.

The first curve 10 in diagram A represents the behavior of the sensor with a fresh, not yet aged sensitive element. The second curve 11 represents the behavior of the sensor with an aged sensitive element. The curves 10, 11 were recorded with a first radiation intensity $I_1$. The third curve 12 illustrates how the phase angle as a function of oxygen concentration changes over the life of a sensitive element if the sensor is operated at an intensity $I_2$ which is reduced in comparison to the two other curves 10 and 11, wherein in this example the radiation intensity was reduced to about ⅕ of the first radiation intensity $I_1$.

As diagram A clearly demonstrates, a sensor with an aged sensitive element has a phase angle which is shifted, i.e. reduced in comparison to the same sensor with a fresh sensitive element. This is made particularly evident by the concentration-dependent measurement error which is shown as curve 13 in diagram B.

The deviation of the third curve 12 from the first curve 10 which was recorded with the fresh sensitive element is clearly smaller than the deviation of the second curve 11 which was recorded with the aged sensitive element. This leads to the conclusion that if a sensitive element is operated at a reduced radiation intensity, its aging process can be slowed down and, accordingly, its service life can be significantly extended. The method relies on this fact, adding the concept that the radiation intensity is adaptively changed during a process, so that even rapid changes of the raw signal can be detected which occur as a result of changes in the measurement medium.

The curves in diagram B represent the concentration-dependent measurement error which can be derived from the curves 10, 11, 12 shown in diagram A. Curve 13 shows the measurement error for the aged sensitive element which was measured under a first radiation intensity $I_1$. Curve 14 shows the measurement error for the sensitive element which was operated with a second, lower radiation intensity $I_2$.

As is made evident by diagram B, with an aged sensitive element the error increases with increasing oxygen concentration, so that if a non-calibrated sensor is operated with an aged sensitive element, the oxygen content or oxygen concentration as calculated from the phase angle will have an increasing error.

In contrast, with the use of a reduced radiation intensity, the error is clearly smaller and the measurement accuracy is considerably better than with an aged sensitive element under a stronger radiation intensity.

FIG. 5 represents two measurement curves which illustrate the time-dependent determination of an oxygen concentration. The aforementioned sensor Mettler-Toledo InPro6870i with a fresh sensitive element was ventilated in a measuring cell, first with air and then with nitrogen, at room temperature and ambient barometric pressure, while at the same time the oxygen concentration as well as the response time were determined. The trail of data points 15 represents the phase angle values of the raw signals. At the beginning of the measurement, the raw signals were measured at a first, higher radiation intensity $I_1$. The vertical line indicates the time when the radiation intensity was set to a second, lower level $I_2$ and the filtering or smoothing was adjusted simultaneously, in accordance with the method as described in the context of FIG. 3.

The smoothed, processed signals are shown in the solid curve 16 which illustrates the advantages of the inventive method.

The processed signals can be calculated for example with a conventional filter function which is referred to as exponential smoothing.

According to the concept of exponential smoothing, a new processed signal $y_n$ is obtained as a function of the current raw signal $x_n$, the preceding processed signal $y_{n-1}$, and a smoothing factor $\alpha$ which lies in the range $0 \leq \alpha \leq 1$, according to the equation $$y_n = \alpha \cdot x_n + (1-\alpha) \cdot y_{n-1}$$

For $\alpha=1$, the processed signal $y_n$ equals the raw signal $x_n$, i.e., no smoothing takes place. As already mentioned above, when the raw signal $x_n$ is undergoing fast and large changes, essentially no smoothing is applied, in order to avoid a slowing-down of the response which would be caused by the smoothing. Such a change was simulated for the measurement in FIG. 5 by the switch from air to nitrogen. As soon as the measurement medium was stable, the radiation intensity was reduced and the filter function was at the same increased. For example the solid curve in FIG. 5 was generated with smoothing factors $\alpha$ in an approximate range of $0.03 \leq \alpha \leq 0.1$. The measurements were taken by means of the method.

As clearly demonstrated in FIG. 5, the lowering of the radiation intensity can in essence be fully compensated by the increased filtering.

The measurements with an oxygen sensor as illustrated in FIGS. 4 and 5 thus demonstrate that, in spite of the adjustment of the radiation intensity and the accompanying adjustment of the smoothing factor or the filter function, the measurement accuracy could be improved, the aging of the sensitive element could be significantly slowed down and, consequently, the service life of the sensitive element could be vastly extended.

As explained in the context of FIG. 3, as an additional possibility the smoothing factor $\alpha$ which enters into the filter function for the calculation of a processed signal $y_n$ from a raw signal $x_n$ can likewise be adaptively adjusted. FIG. 6 represents the time-dependent determination of the oxygen concentration with a sensor of the type InPro6870i which was operated in accordance with the method described in FIG. 3. The sensor was ventilated in a measuring cell, first with air and then with nitrogen, at room temperature and ambient barometric pressure. Next, raw signals were recorded and the response time of the sensor was determined. The data points 16 represent the measured raw signals.

The curves 17, 18 represent the processed signals that were calculated from the raw signals. The calculation of the processed signals for the curve 17 was performed by taking the average over the second and third quartiles. This kind of filter function is referred to as "moving average" and represents a conventional, frequently used filter function. The calculation for the curve 18 is performed by exponential smoothing with a variable or adaptive smoothing factor in accordance with the inventive method. For the smoothing function, the aforementioned exponential smoothing formula was used, wherein the smoothing factor was adaptively adjusted. The adjustment of the smoothing factor followed the procedures that have already been described.

As can be easily be seen in FIG. 6, an adaptive adjustment of the radiation intensity and the smoothing factor has, in comparison to the use of a moving-average filter function, essentially no influence on the response time of the sensor.

Although the invention has been described by presenting specific examples of embodiments, it is considered self-evident that numerous further variants could be created based on the teachings of the present invention, for example by combining the features of the individual embodiments with each other and/or interchanging individual functional units between the embodiments.

What is claimed is:

1. A method for operating a device that optochemically senses an analyte, the device comprising a radiation source that emits radiation of a first and a second predetermined intensity, a detector, and a sensitive element that comprises a signal substance based upon the analyte, the method comprising the steps of:
contacting the sensitive element with the analyte, effecting interaction of the signal substance therewith;
determining a first raw signal, representing a function of the analyte content at a first point in time, by exciting the signal substance with radiation of the first predetermined intensity, generating a signal that is collected by the detector; and
iteratively controlling the device for a predetermined number of iterations, comprising the steps of:
determining a subsequent raw signal, representing a function of the analyte content at a subsequent point in time, by exciting the signal substance with radiation from the radiation source, generating a signal that is collected by the detector;
calculating a comparison value, defined as a change over time of at least two of the raw signals, by the steps of:
applying at least one filter function to convert each of the raw signals into a corresponding processed signal, the filter function having a smoothing factor that enters into the conversion; and
calculating the comparison value as a change over time of at least two of the corresponding processed signals rather than the raw signals;
comparing the calculated comparison value to a predetermined first limit value and adjusting the radiation intensity by the steps of:
when the calculated comparison value is greater than or equal to the predetermined limit value:
setting the radiation source at the first predetermined intensity; and
evaluating and adjusting the smoothing factor; and
when the calculated comparison value is smaller than the predetermined limit value and the analyte content is essentially stable:
calculating a further comparison value defined as a change over time of at least two of the raw signals;
comparing the further comparison value to a predetermined second limit value by the steps of:
when the further comparison value is greater than or equal to the predetermined second limit value, increasing the smoothing factor by a given increment to lessen the effect of the filter function; or
when the further comparison value is smaller than the predetermined limit value, decreasing the smoothing factor by a given increment to increase the effect of the filter function, comparing the smoothing factor to a predetermined reference smoothing factor; and, if the smoothing factor is smaller than or equal to the predetermined reference smoothing factor and the analyte content is essentially stable, setting the radiation source to the second predetermined intensity.

2. The method of claim 1, wherein:
the smoothing factor is selected and adjusted based upon the radiation intensity that is being used.

3. The method of claim 1, wherein:
the comparison value is calculated as a mean value of the two most recent processed signal.

4. The method of claim 1, wherein:
the filter function comprises an exponential smoothing.

5. The method of claim 1, further comprising the step of:
calculating the remaining service life of the sensitive element.

6. The method of claim 1, wherein:
the smoothing factor is selected and adjusted as a function of the intensity of the radiation source that was used to generate the raw signal.

7. A method for operating a device that optochemically senses an analyte in a medium, the device comprising a radiation source that emits radiation of a first and a second predetermined intensity, the second predetermined intensity being lower than the first predetermined intensity, a detector, and a sensitive element that comprises a signal substance based upon the analyte, the method comprising the steps of:
contacting the sensitive element with the medium, effecting interaction of the signal substance therewith;
determining a first raw signal, representing a function of the analyte content of the medium at a first point in time, by exciting the signal substance with the radiation source set at the first predetermined intensity, generating a signal that is collected by the detector; and
iteratively controlling an instant level of the radiation intensity based upon the analyte content of the medium, starting with the instant level at the first predetermined intensity, by the steps of:
determining at least one subsequent raw signal, each subsequent raw representing a function of the analyte content at a subsequent point in time, by exciting the signal substance with radiation at the instant level of the predetermined intensity, generating a signal that is collected by the detector;
determining the stability of the signals being obtained by the steps of:
applying at least one filter function to convert each of the raw signals into a processed signal, wherein the filter function comprises a smoothing factor;
calculating a first comparison value as a change over time of the processed signals;
calculating a second comparison value as a change over time of the raw signals; and
based upon the calculated first comparison value:
setting the instant level to the first predetermined intensity if the comparison value is equal to or exceeds a first predetermined limit value, indicating the analyte content is not stable; or
setting the instant level at the second predetermined intensity if the first comparison value is smaller than the first predetermined limit value, indicating the analyte content is stable; and
adjusting the smoothing factor based on a comparison of the calculated second comparison value to a second predetermined limit value.

* * * * *